Figure 1:
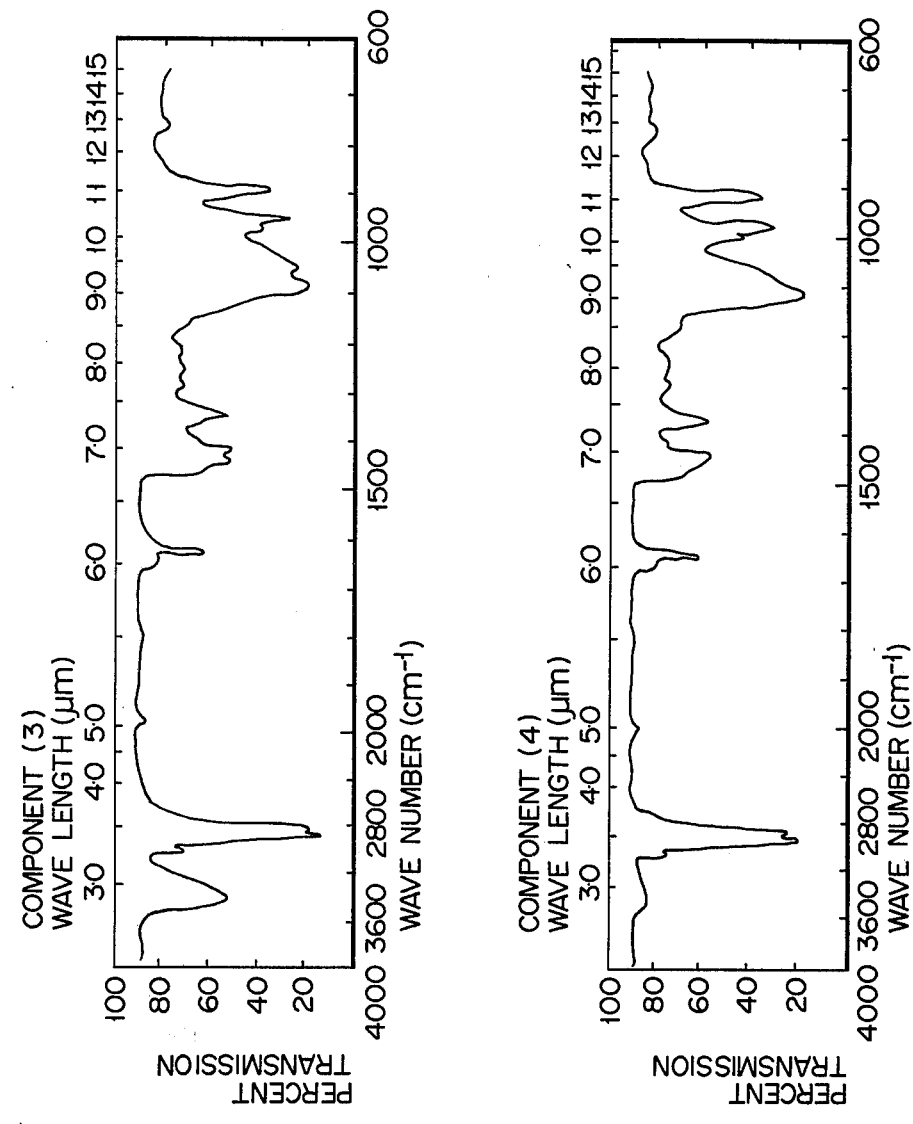

United States Patent [19]

Enomoto et al.

[11] 4,006,192
[45] Feb. 1, 1977

[54] 1,1-DI-(2,7 OCTADIENEOXYMETHYLENE)-1-(HYDROXYMETHYLENE)ALKANE

[75] Inventors: Satoru Enomoto, Fujisawa; Hitoshi Takita, Tokyo; Mikiro Yanaka, Matsudo; Yutaka Mukaida; Hisayuki Wada, both of Tokyo, all of Japan

[73] Assignee: Kureha Kagaku Kogyo Kabushiki Kaisha, Tokyo, Japan

[22] Filed: Dec. 23, 1974

[21] Appl. No.: 535,697

[30] Foreign Application Priority Data

Dec. 27, 1973    Japan .......................... 49-144302

[52] U.S. Cl. .................. 260/615 R; 252/52 R; 252/49.8; 260/75 R; 260/78.41; 106/252
[51] Int. Cl.² ........................................ C07C 43/02
[58] Field of Search ................ 260/615 R, 614 AA

[56] References Cited

UNITED STATES PATENTS 3,499,042   3/1970   Smutny ...................... 260/614 AA

FOREIGN PATENTS OR APPLICATIONS 47-20204     6/1972    Japan .......................... 260/614 AA
1,256,357   12/1971    United Kingdom ........ 260/614 AA
1,248,592   10/1971    United Kingdom ........ 260/614 AA

*Primary Examiner*—Howard T. Mars
*Attorney, Agent, or Firm*—Flynn & Frishauf

[57] ABSTRACT

1,1-di-(2,7 octadieneoxymethylene)-1-(hydroxymethylene)alkane prepared by reacting trimethylol compounds with butadiene, using a catalyst consisting of palladium compounds, alkali metal salts of weak acids and phosphines, said alkane being important as a chemical intermediate in manufacturing lubricating oils and paints.

2 Claims, 2 Drawing Figures

COMPONENT (3)

$\delta$; 5.2~6.2(m, =CH-)
4.7~5.2(m, =CH$_2$)
3.86(d, J=4Hz, =C-CH$_2$-O-)
3.48(S, -C-CH$_2$-O-)
3.30(S, -OCH$_2$-C-CH$_2$O-)
2.88(S, -OH)
1.8~2.3(m, =C-CH$_2$-C-)
1.1~1.7(m, -CCH$_2$C-, CH$_3$CH$_2$-)
0.82(t, J=6.5Hz, CH$_3$-)

COMPONENT (4)

$\delta$; 5.2~6.2(m, =CH-)
4.7~5.2(m, =CH$_2$)
3.81(d, J=4Hz, =CCH$_2$O-)
3.20(S, -OCH$_2$C-CH$_2$O-)
CH$_2$O-
1.8~2.3(m, =C-CH$_2$-C-)
1.1~1.7(m, -CCH$_2$C-, -CH$_2$CH$_3$)
0.81(t, J=6.5Hz, CH$_3$-)

1,1-DI-(2,7 OCTADIENEOXYMETHYLENE)-1-(HYDROXYMETHYLENE)ALKANE

This invention relates to novel unsaturated aliphatic ether compounds and more particularly to 1,1-di-(2,7 octadieneoxymethylene)-1-(hydroxymethylene)alkane. "Bulletin of the Chemical Society, Japan," 41, 454, 1968 and the Japanese Patent Publication 20,204, 1972 issued on June 8, 1972 disclose that monoctadienyl derivatives can be synthesized by reacting butadiene with alcohols of relatively low molecular weight such as methanol, ethanol and ethylene glycol. To date, however, no technique has been reported of obtaining compounds containing two or more octadienyl radicals in good yield.

It is accordingly an object of this invention to provide novel unsaturated aliphatic ether compounds containing two or more octadienyl radicals.

Another object of the invention is to provide a method of producing 1,1-di-(2,7 octadieneoxymethylene)-1-(hydroxymethylene)alkanes.

Still another object of the invention is to provide an effective catalyst for manufacture of the above-mentioned novel unsaturated aliphatic ether compounds.

Said novel compounds can be prepared by reacting trimethylol compounds with butadiene using a catalyst prepared from palladium compounds, alkali metal salts of weak acids and phosphines.

Figure 2:
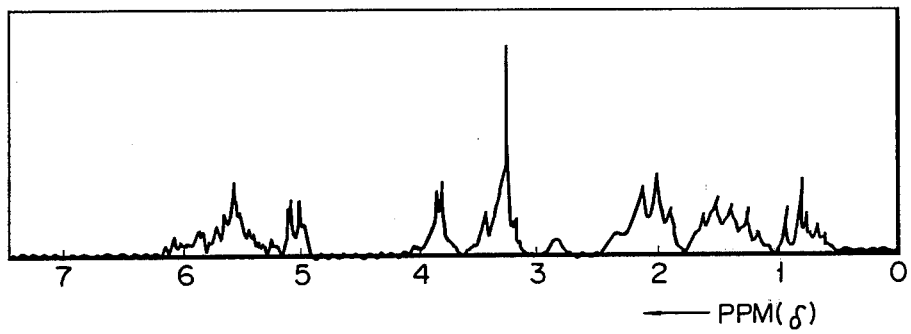
Figure 2:
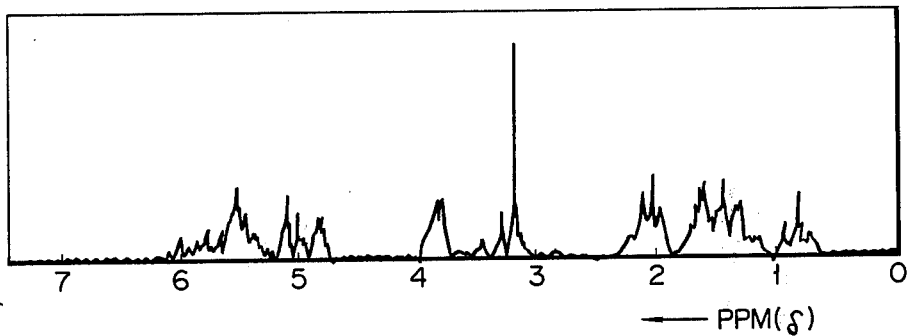

This invention can be more fully understood from the following detailed description when taken in conjunction with the accompanying drawing, in which:

FIG. 1 shows the infrared spectra of two types (3) and (4) of the subject product prepared in Example 1; and FIG. 2 indicates the nuclear magnetic resonance spectra (NMR) of said two types (3) and (4) of the subject product.

The palladium compounds used in this invention include palladium halides, palladium salts of inorganic and organic acids and $\pi$ aryl palladium halides. Most practically useful among these palladium compounds are palladium chloride, palladium nitrate and palladium acetate.

The phosphines used in the invention include alkyl phosphines, arylphosphines, etc. Generally, however, triphenyl phosphine can be easily used.

The weak acids are chosen to be those having an electric dissociation exponent ranging between 4 and 11, or generally organic acids and phenols. Most common among the alkali metal salts of these weak acids are sodium benzoate, sodium acetate and sodium phenolate.

The trimethylol compounds used in the invention are those containing three CH$_2$OH radicals. Most preferred for the object of the invention, however, are trimethylol alkanes, particularly trimethylol propane.

When reacted with trimethylol compounds, butadiene is used in an amount of 1 to 15 mols, preferably 2 to 11 mols per mol of the trimethylol compounds. Where butadiene is applied in a smaller amount than an equivalent mol, then the reaction system will still contain unreacted trimethylol compounds. Conversely where the proportion of butadiene exceeds 15 mols, then a prominent amount of butadiene dimer will be undesirably produced in addition to the adduct of octadienyl. The palladium compound is chosen to have a concentration of $10^{-3}$ to $10^{-5}$ mol per mol of the butadiene. The phosphine is desired to have a concentration of 1 to 5 mols per mol of the palladium compound. The alkali metal salt of weak acid is used in a proportion of more than 5 mols, as 5 to 200 mols, or preferably 10 to 200 mols per mol of the palladium compound.

Reaction is carried out at a temperature ranging between room temperature and 200° C, or preferably between about 50° and about 150° C, and for a shorter period than 20 hours.

While the above-mentioned method of this invention provides in good yield compounds containing two octadienyl radicals, namely, 1,1-di-(2,7 octadieneoxymethylene)-1-(hydroxymethylene)alkane, there is also obtained a by-product of 1,1,1-tri-(2,7 octadieneoxymethylene)alkane, or a novel compound containing three octadienyl radicals. This by-product is also a novel compound unpublished in literature, and has been disclosed in this application for the first time.

A 1,1-di-(2,7 octadieneoxymethylene)-1-(hydroxymethylene) alkane is a high boiling liquid containing four double bonds in the molecule, and can be widely applied as an intermediate in carrying out various organic synthesis reactions or making high molecular materials. For example, hydrogenation of the double bonds provides lubricating oil having low flow point and excellent viscosity-temperature characteristics. Further, reaction between the hydrogenated subject compound and diaryl monochlorophosphate or dicresyl monochlorophosphate provides a self-extinguishing lubricating oil. Esterification of the above-mentioned unsaturated oxyether in the presence of dibasic carboxylic acids such as isophthalic acid or maleic acid, polyols such as ethylene glycol or unsaturated carboxylic acids can provide modified alkyd resins. These modified alkyd resins, when mixed with a drying oil, are very favorably accepted as paints.

An 1,1-di-(2,7 octadieneoxymethylene)-1-(hydroxymethylene) alkane of this invention is obtained by further purification. Depending on application, however, it is possible to use the unpurified form of said compound containing one to three octadienyl radicals.

This invention will be more fully understood by reference to the examples which follow.

EXAMPLE 1

A 1l autoclave was charged with 83.1g (0.62 mol) of trimethylol propane, 1.97g (22.1 m mol) of sodium acetate and 0.276g (0.37 m mol) of a complex compound consisting of palladium acetate and triphenyl phosphine, wherein the palladium acetate had a molar ratio of ½ to the triphenyl phosphine. After being purged with nitrogen, the autoclave was further charged with 200g (3.7 mols) of liquefied butadiene. Reaction was continued 6 hours with stirring at 83° C, providing 253g of the reaction product, which, upon distillation, was found to consist of four components shown in Table 1.

Table 1

| Component | Boiling point (° C/mm Hg) | Weight (g) | Wt % |
|---|---|---|---|
| (1) | 125/760 | 60.8 | 24.0 |
| (2) | 125 to 160/2 | 27.8 | 11.6 |
| (3) | 188.5 to 193.5/2 | 159.5 | 63.0 |
| (4) | 203 to 218/0.5 | 4.5 | 1.8 |

The component (1) is butadiene dimer and the component (2) is a compound containing one octadienyl radical. The component (3), (4) are compounds having refractive indices of 1.4769 and 1.4800, respectively, and molecular weights of 320 and 420, respectively, as measured by the VPO method. The components (3) and (4) indicated infrared and nuclear magnetic resonance spectra given in FIGS. 1 and 2. As apparent from the above, it has been disclosed that the component (3) is 1,1-di-(2,7 octadieneoxymethylene)-1-(hydroxymethylene) propane having a chemical structure expressed by the formula:

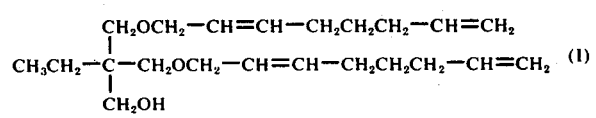

and a theoretical molecular weight of 350, and that the component (4) is 1,1,1-tri-(2,7 octadieneoxymethylene) propane having a chemical structure expressed by the formula:

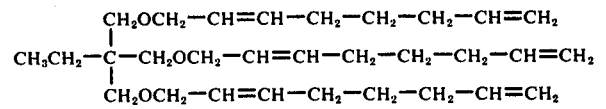

and a theoretical molecular weight of 458. The trimethylol compounds were converted at the rate of substantially 100% and the butadiene at the rate of 85%.

The above-mentioned two components (3), (4) presented the following element analyses:
I. C 75.42%, H 10.86%, O 13.71%
II. C 78.60%, H 10.92%, O 10.48%

EXAMPLES 2 TO 4

An autoclave was charged with the same amounts of trimethylol propane and butadiene as in Example 1. Reaction was continued 6 hours with stirring at 87° C by changing the catalyst composition as shown in Table 2 below, obtaining the results given therein. The trimethylol propane was converted at a higher rate than 95% in all cases.

EXAMPLE 5

An autoclave was charged with 53.2g (0.40 mol) of trimethylol propane, 216g (4.0 mol) of butadiene, 0.28g (0.4 m mol) of a complex compound, namely, $PdCl_2[(C_6H_5)_3P]_2$ prepared from 0.0706g (0.40 m mol) of $PdCl_2$ and 0.210 g (0.8 m mol) of triphenyl phosphine, and 2.79g(24.0 m mol) of $C_6H_5ONa$ in the same manner as in Example 1. Reaction was continued 5 hours at 87° C. The component (3) of the reaction product indicating the chemical analysis (I) accounted for 49.1% and the component (4) indicating the chemical analysis (II) amounted to 2.5%. In this case, low boiling components contained in the reaction product consisted of 42% of 1,3,7octatriene and 4.6% of 1-(2,7 octadieneoxymethylene)-1,1-di-(hydroxymethylene)-propane. Substantially no unreacted trimethylol propane appeared.

EXAMPLE 6

A 1l autoclave was charged with 84g (0.7 mol) of trimethylol ethane, 2.32g (20 m mol) of sodium phenolate and 0.30g (0.4 m mol) of a complex compound of palladium acetate and triphenyl phosphine prepared from 0.085g (0.4 m mol) of palladium acetate and 0.2098g (0.8 m mol) of triphenyl phosphine. The autoclave was further charged with 226g (4.2 mols) of liquefied butadiene. Reaction was continued 6 hours at 90° C. Thereafter the reaction system was distilled, providing 205 g of 1,1-di-(2,7 octadieneoxymethylene)-1-(hydroxymethylene)ethane and 16g of 1,1,1-tri-(2,7 octadieneoxymethylene)ethane, and 45g of octatriene.

What we claim is:
1. 1,1-di-(2,7 octadieneoxymethylene)-1-(hydroxymethylene)propane.
2. 1,1-Di-(2,7-octadieneoxymethylene)-1-(hydroxymethylene)ethane.

* * * * *

Table 2

| Example | Palladium compound | phosphine | Alkali metal salt of weak acid | Wt % I | II |
|---|---|---|---|---|---|
| 2 | 0.0853g (0.38 m mol) of palladium acetate | 0.1993g (0.76 m mol) of triphenyl phosphine | 2.67g (23 m mol) of sodium phenolate | 69.9 | 1.4 |
| 3 | 0.0706g (0.40 m mol) of palladium chloride | 0.210g (0.80 m mol) of triphenyl phosphine | 1.886g (23 m mol) of sodium acetate | 48.2 | 0.9 |
| 4 | 0.076g (0.40 m mol) of palladium chloride | 0.2098g (0.80 m mol) of triphenyl phosphine | 3.0186g (26 m mol) of sodium phenolate | 59.5 | 7.6 |

Note:
The character I in Table 2 above denotes 1,1-di-(2,7 octadieneoxymethylene)-1-(hydroxymethylene) propane.
The character II represents 1,1,1-tri-(2,7 octadieneoxymethylene) propane.